United States Patent [19]

Shepard et al.

[11] 4,229,455

[45] Oct. 21, 1980

[54] IMINO-BRIDGED BENZOCYCLOHEPTAPYRIDINES

[75] Inventors: Kenneth L. Shepard, Ambler; Wasyl Halczenko, Hatfield, both of Pa.

[73] Assignee: Merck & Co., Inc., Rahway, N.J.

[21] Appl. No.: 952,354

[22] Filed: Oct. 18, 1978

Related U.S. Application Data

[63] Continuation-in-part of Ser. No. 944,431, Sep. 21, 1978, abandoned, which is a continuation-in-part of Ser. No. 860,666, Dec. 15, 1977, abandoned.

[51] Int. Cl.$^2$ ............... C07D 471/08; A61K 31/44
[52] U.S. Cl. ............................ 424/256; 542/455; 546/63; 546/72; 546/110
[58] Field of Search ............... 546/63, 72, 101; 424/256

[56] References Cited

U.S. PATENT DOCUMENTS

| | | | |
|---|---|---|---|
| 3,641,038 | 2/1972 | Davis et al. | 546/72 |
| 3,716,541 | 2/1973 | Dobson et al. | 546/72 |
| 4,052,508 | 10/1977 | Anderson et al. | 546/101 |
| 4,064,139 | 12/1977 | Anderson et al. | 260/313.1 |
| 4,123,546 | 10/1978 | Haire | 424/274 |

OTHER PUBLICATIONS

Villani et al., J. Het. Chem., vol. 8, pp. 73–81 (1971).
Villani et al., J. Het. Chem., vol. 9, pp. 1203–1207 (1972).
Price, Mechanisms of Reactions at Carbon–Carbon Double Bonds, pp. 46 to 47, Interscience Publishers, Inc. NY (1946).

*Primary Examiner*—John D. Randolph
*Attorney, Agent, or Firm*—Mario A. Monaco; William H. Nicholson

[57] ABSTRACT

Benzocycloheptapyridines with an imine bridge in the cycloheptane ring, derivatives and pharmaceutically acceptable salts thereof are useful as antianxiety agents, as muscle relaxants and in the treatment of extrapyramidal disorders such as in Parkinson's disease.

6 Claims, No Drawings

IMINO-BRIDGED BENZOCYCLOHEPTAPYRIDINES

BACKGROUND OF THE INVENTION

This is a continuation-in-part of application Ser. No. 944,431, filed Sept. 21, 1978, which in turn is a continuation-in-part of Application Ser. No. 860,666, filed Dec. 15, 1977, both are now abandoned.

This invention is concerned with novel benzocycloheptapyridines with an imine bridge in the cycloheptane ring, derivatives and pharmaceutically acceptable salts thereof which are useful as anti-anxiety agents, muscle relaxants, and in the treatment of extrapyramidal disorders such as in Parkinson's disease.

Structurally related compounds are known in the art to have qualitatively similar utilities. For example U.S. Pat. No. 3,892,756 discloses 10,11-dihydro-5H-dibenzo[a,d]cyclohepten-5,10-imine and derivatives; and Belgian Pat. No. 829,075 discloses 9,10-dihydroanthracen-9,10-imines and derivatives.

It is an object of this invention to provide the novel compounds, novel processes for their synthesis, pharmaceutical compositions comprising them as active ingredient, and a novel method of treatment where there is an indicated need for an antianxiety agent, muscle relaxant, or a treatment for extrapyramidal disorders.

DETAILED DESCRIPTION OF THE INVENTION

The novel compounds of this invention have structural formulae:

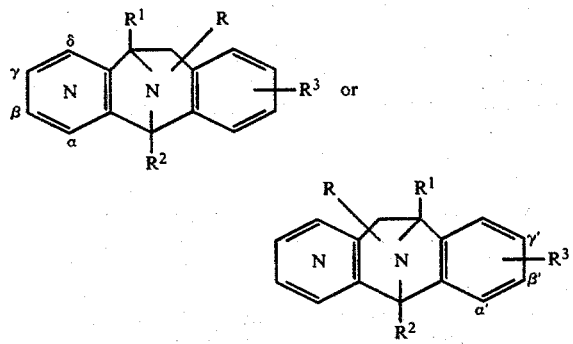

or a pharmaceutically acceptable salt thereof, wherein $R^1$ and $R^2$ are independently,
(1) hydrogen,
(2) lower alkyl, especially $C_{1-5}$ alkyl, preferably methyl or ethyl,
(3) lower alkenyl, especially $C_{2-5}$ alkenyl, preferably vinyl or allyl,
(4) phenyl-lower alkyl, especially phenyl-$C_{1-3}$ alkyl, preferably benzyl,
(5) lower cycloalkyl, especially $C_{3-6}$ cycloalkyl, preferably cyclopropyl or cyclohexyl,
(6) lower(cycloalkyl-alkyl), especially $C_{3-6}$ cycloalkyl-$C_{1-3}$ alkyl,
with the proviso that only one of $R^1$ and $R^2$ is other than hydrogen; R is
(1) $R^2$,
(2) phenyl, or
(3) di(lower alkyl)amino-lower alkyl, especially di($C_{1-3}$ alkyl)amino-$C_{1-5}$ alkyl; and $R^3$ is
(1) hydrogen,
(2) halogen, such as chloro, bromo, fluoro, or iodo,
(3) lower alkoxy, especially $C_{1-5}$ alkoxy, preferably methoxy,
(4) trifluoromethylthio,
(5) cyano, or
(6) carboxy.

It is preferred that the nitrogen of the pyridine ring be in the $\alpha$, $\beta$ or $\delta$ position, and most preferably in the $\beta$-position.

Another preferred group of compounds is that wherein $R^3$ is hydrogen.

Where $R^3$ is other than hydrogen, it is preferred that it occupy the $\beta$ and/or $\gamma'$ positions of the tricyclic ring system.

Preferred definitions for R, $R^1$ and $R^2$ are hydrogen, lower alkyl, especially methyl, or benzyl.

The novel compounds of this invention are generally preparable by formation of the imine bridge by addition of an amino group attached to the seven membered ring across a double bond, also in the seven membered ring. The reaction is accomplished by treating the amino compound in an inert solvent such as a lower alkanol such as ethanol, propanol, butanol, or a chlorinated hydrocarbon such as chloroform or the like in the presence of an acid until the ring closure is complete. Reaction times of a few minutes to several days are employed depending on the structure of the particular starting material.

Temperatures from about 15° C. to about 150° C. or reflux temperatures can be employed. Where $R^1$ is other than hydrogen, the reaction proceeds readily at the lower temperatures. The acid can be a hydrogen halide or other anhydrous inorganic or organic acid such as trifluoroacetic acid, and where $R^1$ is other than hydrogen, chromatography of the starting material on silica gel with chloroform is sufficiently acidic to cause the cyclization.

An alternate procedure of forming the imine bridge comprises treating a compound with a bromo and an oxo group in the seven-membered ring with an amine at about 10° C. to about 20° C. in an inert organic solvent such as tetrahydrofuran, dimethoxyethane, acetonitrile, DMF or the like for 5 to about 36 hours. This results in displacement of the bromo group by the amino group followed by spontaneous addition across the oxo function. The hydroxyl function that is formed in the reaction is converted to a chloro group by treatment with thionyl chloride in an inert solvent such as benzene, toluene or the like at 10° C. to about 100° C. for 15 minutes to about 2 hours. The resulting chloro group is then hydrogenolyzed by catalytic hydrogenation, such as with 40 to 50 p.s.i. of hydrogen in the presence of a palladium, platinum, or the like, hydrogenation catalyst at about 10° C. to about 30° C. until the theoretical amount of hydrogen is consumed.

Alternatively, particularly wherein $R^3$ is halo, the hydrogenalysis is accomplished with a complex metal hydride such as lithium aluminum hydride or sodium borohydride.

The novel compounds of this invention wherein R is hydrogen are generally prepared by reduction of the N-hydroxy analog. The preferred reducing agent is nascent hydrogen generated by the action of a metal, preferably zinc with an acid such as acetic acid at 40° to 100° C. for 1 to about 10 hours.

Where R is other than hydrogen, the novel compounds may be prepared by alkylation of these compounds wherein R is hydrogen with the appropriate reagent of formula R-halo wherein halo represents chloro, bromo or iodo. The reaction is normally conducted in an inert solvent such as benzene, or toluene. However, the alkylating reagent, depending on its physical properties, may be used in sufficiently excess amount to act as solvent. It is preferred to conduct the reaction in the presence of an acid acceptor such as an inorganic carbonate such as sodium carbonate, an organic base such as pyridine, or a basic resin. Temperatures of about 50° C. to about 100° C. may be employed over reaction times of about 10 hours to about 5 days.

Where R is alkyl or substituted alkyl, the compounds also may be prepared by reduction of an N-acyl compound such as alkoxycarbonyl to give methyl or other alkanoyl groups to provide the other alkyl groups. The preferred reducing system is a metal hydride such as lithium aluminum hydride in an ethereal solvent such as ether, tetrahydrofuran or 1,2-dimethoxyethane or the like. The reaction proceeds satisfactorily at room temperature but temperatures from about 0° C. to about 50° C. are appropriate with reaction times of 10–13 hours.

An additional alkylation method involves the treatment of the unsubstituted imine with an aldehyde and sodium cyanoborohydride (NaCNBH$_3$) in an ether such as tetrahydrofuran, 1,2-dimethoxyethane or di(2-methoxyethyl)ether, preferably tetrahydrofuran, at about 10°–50° C., preferably 25° C., until the reaction is substantially complete, usually for about 6 hours to about 3 days, preferably about 2 days.

Novel compounds having a substituent on the benzenoid ring are generally prepared by metathesis of the appropriate bromo or iodo compound. For example treatment with an alkali metal lower alkoxide such as a sodium lower alkoxide in the presence of copper dust in a solvent such as dimethyl formamide at 50°–150° C. for 1–10 hours yields the corresponding lower alkoxy compound.

Similarly treatment of a bromo or iodo compound with cuprous cyanide in a solvent such as dimethyl formamide at reflux temperature for 1–10 hours yields the corresponding cyano compound.

Hydrolysis of the above cyano compounds with a mineral acid such as hydrochloric acid at reflux temperature produces the corresponding carboxy substituted compounds.

Also treatment of the bromo or iodo compounds with bis(trifluoromethylthio)mercury and copper dust or trifluoromethylthio-copper in a solvent such as dimethyl formamide or hexamethylphosphoric acid triamide at about 100°–200° C. for 1–10 hours yields the trifluoromethylthio derivatives.

The starting materials and processes used for preparing the intermediates used in the above described processes are fully described in the Examples.

Also included within the scope of the present invention are the non-toxic pharmaceutically acceptable salts of the novel compounds. Acid addition salts of the imine are formed by mixing a solution of the imine with a solution of a pharmaceutically acceptable non-toxic acid such as hydrochloric acid, fumaric acid, maleic acid, succinic acid, acetic acid, citric acid, tartaric acid, phosphoric acid, or the like. Where the novel compound carries a carboxylic acid group, the invention also contemplates sodium, potassium, and calcium salts thereof.

The novel compounds can be resolved into their optical isomers by standard techniques, such as the formation of diastereomeric pairs by salt formation with an optically active acid, such as (−)di-p-toluoyl-d-tartaric acid and/or (+)-di-p-toluoyl-1-tartaric acid followed by fractional crystallization and regeneration of the free base.

In the method of treatment aspect of the present invention, the novel imines are capable of producing anxiety relief without causing excessive sedation or sleep at a dosage level of from about 0.01 to about 10 mg. per kilogram of body weight preferably about 0.5–5 mg/kg. of body weight on a regimen of 1–4 times a day. In addition, the novel compounds of the present invention are useful as muscle relaxants, anticonvulsants and in the treatment of extrapyramidal disorders when indicated at comparable dosage levels. It is understood that the exact treatment level will depend upon the case history of the animal or human individual being treated and in the last analysis the precise treatment level falling within the above guidelines is left to the discretion of the therapist.

Also included within the scope of the present invention are pharmaceutical compositions comprising the imines of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, i.e., conventional tableting ingredients such as corn starch, lactose, sucrose, sorbitol, talc, stearic acid, magnesium stearate, dicalcium phosphate, gums, and other pharmaceutical diluents, e.g., water, to form a solid preformulation composition containing a homogeneous mixture of an imine of the present invention, or a non-toxic pharmaceutically acceptable salt, thereof. When referring to these preformulation compositions as homogeneous, it is meant that the active ingredient, is dispersed evenly throughout the composition so that the composition may be readily subdivided into equally effective unit dosage forms such as tablets, pills, capsules, and the like. This solid preformulation composition is then subdivided into unit dosage forms of the type described above containing from 0.1to about 500 mg. of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like.

The liquid forms in which the novel composition of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, gelatin and the like.

EXAMPLE 1

5,6-Dihydro-6,12-dimethylbenzo[5,6]cyclohepta[1,2-c]pyridin-6,11-imine

Step A: Preparation of trans-4-(α-methylstyryl) nicotinamide t-Butyl alcohol (29.6 g.) is added to a suspension of sodium hydride (12.6 g., 57% oil dispersion) in dimethylformamide (300 ml.) and the resulting mixture is warmed on the steam bath until hydrogen evolution ceases. The resulting stirred solution is cooled to 0° C. and a solution of 23.6 g. of 4-methylnicotinonitrile in dimethylformamide (100 ml.) is added dropwise (0.5–1 hour). The mixture is stirred at this temperature for an additional hour and a solution of acetophenone (24 g.) in dimethylformamide (100 ml.) is added dropwise. After 24 hours, the reaction mixture is poured over ice and the solution is acidified by the addition of glacial acetic acid. The solid that separates is filtered, washed with water and dried to give 38 g. of trans-4-(α-methylstyryl)nicotinamide, m.p. 150°–155°. Recrystallization from ethyl acetate produces product of m.p. 153.5°–155.5°.

Step B: Preparation of trans-4-(α-methylstyryl)nicotinc acid

A mixture of trans-4-(α-methylstyryl)nicotinamide (5.1 g.), potassium hydroxide (5 g.), ethanol (50 ml.), and water (50 ml.) is heated under reflux for 24 hours. The ethanol is removed by distillation and the resulting aqueous solution is chilled and acidified by the addition of glacial acetic acid (5 ml.). The white solid that separates is filtered, washed with water, and dried to give 4.46 g. of trans-4-(α-methylstyryl)nicotinic acid, m.p. 151°–158° C. Recrystallization from ethanol followed by recrystallization from methanol gives material with m.p. 160°–161.5° C.

Step C: Preparation of 6-methylbenzo[5,6]cyclohepta[1,2-c]pyridin-11-one

Trans-4-(α-methylstyryl)nicotinic acid (7.77 g.) is added to polyphosphoric acid with stirring (210° C.). The temperature of the stirred mixture is raised to 225° C. and maintained at 225°–230° C. for 0.25 hours. After cooling to 50° C. ice and water is added to 600 ml. total volume. The solution is made alkaline by the addition of concentrated aqueous ammonia and the solid that separates on cooling is filtered, washed with water, and dried to give 3.0 g. of 6-methylbenzo[5,6]cyclohepta[1,2-c]pyridin-11-one, m.p. 112°–116° C. Recrystallization from cyclohexane provides material with m.p. 117.5°–119.5° C.

Employing the procedure substantially as described in Example 1, Steps A, B, and C but optionally substituting for the acetophenone used in Step A thereof a corresponding molecular amount of a compound of structure

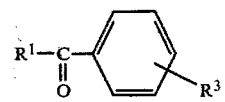

there are obtained the 6-R¹-benzo[5,6]-cyclohepta[1,2-]pyridin-11-ones described in Table I in accordance with the following reaction scheme:

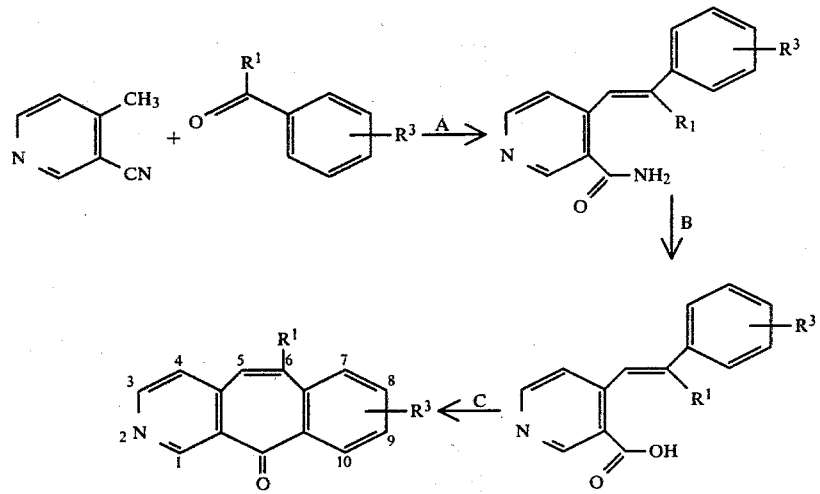

TABLE I

| R¹ | R³ |
|---|---|
| CH₃— | 9-Br |
| n-C₃H₇— | 9-Br |
| CH₂=CH—CH₂— | H |
| ⌬—CH₂— | H |
| ▷— | 9-Br |
| ⬡— | H |

TABLE I-continued

| R¹ | R³ |
|---|---|
| cyclohexyl-CH₂— | 9-Br |
| cyclopropyl-CH₂— | H |
| $C_2H_5$— | 9-F |
| $CH_3$— | 9-F |
| H | 9-Br |
| H | 9-F |

Step D: Preparation of 6-methyl-11-methyliminobenzo[5,6]cyclohepta[1,2-c]pyridine A solution of titanium tetrachloride (0.7 ml., 0.006 mole) in benzene (20 ml.) is added rapidly to a stirred solution of methylamine (1.24 g., 0.04 mole) and 6-methylbenzo[5,6]cyclohepta[1,2-c]pyridin-11-one (2.21 g., 0.01 mole) in benzene (150 ml.). After 4 hours, anhydrous potassium carbonate is added and the reaction mixture is filtered. The filtrate is evaporated to a pale yellow oil, (2.95 g.).

Step E: Preparation of 5,6-dihydro-6,12-dimethylbenzo[5,6]cyclohepta[1,2-c]pyridin-6,11-imine Sodium borohydride (0.20 g.) is added to a solution of 6-methyl-11-methyliminobenzo[5,6]cyclohepta[1,2-c]pyridine (2.95 g.) in acetonitrile (100 ml.). The resulting mixture is heated on the steam bath for 4 hours. Another 0.10 g. of sodium borohydride is added and the mixture is heated for an additional two hours. The solvent is removed under reduced pressure and the residue is dissolved in 3 N HCl (100 ml.). The acidic solution after extraction with ether is made alkaline by the addition of 40% NaOH solution and re-extracted with methylene chloride. After drying, the solvent is removed in vacuo to give an amber oil, (2 g.). This material is chromatographed over 50 g. of silica gel with CHCl₃ and increasing amounts of ethyl acetate. The produce is eluted with ethyl acetate and on evaporation yields a viscous oil, 1.2 g. Trituration with petroleum ether converts the oil to a white solid, m.p. 77°–82°.

Following the procedure substantially as described in Example 1, Steps D and E but substituting for the methylamine used in Step D, an equimolecular amount of a compound of formula R-NH₂ described in Table II, there are produced the 5,6-dihydro-6-R¹-12-R-benzo[5,6]cyclohepta[1,2-c]pyridin-6,11-imines also described in Table II in accordance with the following scheme:

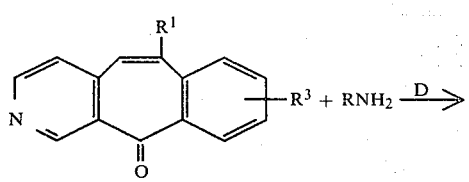

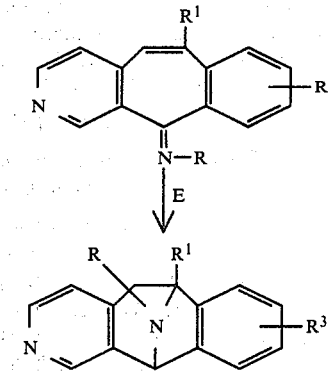

TABLE II

| R¹ | R³ | R |
|---|---|---|
| $CH_3$— | 9-Br | —$CH_3$ |
| $n$-$C_3H_7$ | 9-Br | —$CH_2$—$CH$=$CH_2$ |
| $CH_2$=$CH$—$CH_2$— | H | —$CH_2$—C₆H₅ |
| phenyl-CH₂— | H | —cyclopropyl |
| cyclopropyl- | 9-Br | —$CH_3$ |
| cyclohexyl- | H | —$CH_2$—cyclohexyl |
| cyclohexyl-CH₂— | 9-Br | —$CH_2$—cyclopropyl |
| cyclopropyl-CH₂— | H | —cyclohexyl |
| $C_2H_5$ | 9-F | —$CH_3$ |
| $CH_3$— | 9-F | —$CH_3$ |
| $CH_3$— | H | —$CH_2CH_2N(CH_3)_2$ |
| $CH_3$— | H | —$CH_2CH_2CH_2N(CH_3)_2$ |

EXAMPLE 2

5,6-Dihydro-12-methylbenzo[5,6]cyclohepta[1,2-c]pyridin-6,11-imine dihydrochloride hydrate Step A: Preparation of 11-methylaminobenzo[5,6]cyclohepta[1,2-c]pyridine hydrochloride Methylamine (6.2 g., 0.2 mole) is added to a mechanically stirred mixture of benzo[5,6]cyclohepta[1,2-pyridin-11-one (10 g., 0.048 mole) in benzene (1000 ml.). A solution of TiCl₄ (3.5 ml.) in benzene (100 ml.) is added and the mixture is stirred at 25° C. for 18–24 hours. Anhydrous potassium carbonate is added to the mixture and it is filtered through diatomaceous earth. The filtrate is stripped to an amber oil and this oil is dissolved in acetonitrile (500 ml.). Sodium borohydride (3 g.) is added and the mixture stirred at 25° C. for 18 hours. An additional 0.5 g. of NaBH₄ is added and the mixture is warmed on the steam bath for one hour. Dilute HCl (3 N) is added to the cooled reaction mixture and it is evaporated to dryness under reduced pressure. The residue is dissolved in 3 N HCl (200 ml.), treated with decolorizing carbon and filtered. The filtrate is extracted with ether and the aqueous filtrate is made alkaline by the addition of 20% NaOH solution. The basic material is extracted into CHCl$_3$ and concentrated to an amber oil. The oil is dissolved in 50 ml. of ethanol and treated with 11 N HCl to give 7.75 g. of 11-methylaminobenzo[5,6]cyclohepta[1,2-c]pyridine hydrochloride, m.p. 216°–221° C.

Step B: Preparation of 5,6-dihydro-12-methylbenzo[5,6]cyclohepta[1,2-c]pyridin-6,11-imine dihydrochloride hydrate 11-Methylaminobenzo[5,6]cyclohepta[1,2-c]pyridine hydrochloride is treated with a boiling mixture of methanol and 2-propanol (50:50, 750 ml.) and evaporated to a volume of 250 ml. The solid that separates is filtered, 2.16 g., m.p. 221°–223° C. dec. Spectral investigation indicates this solid to be a mixture of the hydrochloride of 11-methylaminobenzo[5,6]cyclohepta[1,2-c]pyridine and the title compound. The filtrate is evaporated in vacuo and the residue is treated with ethanol (25 ml.) and the solid that separates on standing is collected and dried to give 1.9 g. of product, m.p. 211°–215°. Recrystallization of this solid from ethanol gives 5,6-dihydro-12-methylbenzo[5,6]cyclohepta[1,2-c]pyridin-6,11-imine dihydrochloride hydrate, m.p. 216.5°–218.5° C.

Employing the procedure substantially as described in Example 2, Steps A and B but substituting for the methylamine used in Step A, an equimolecular amount of an amine of formula R—NH$_2$, wherein R is

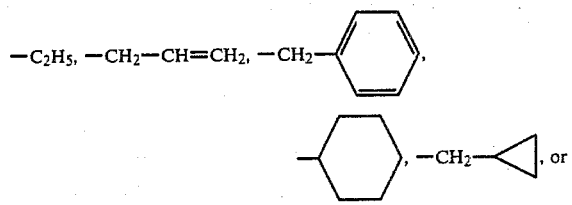

—CH$_2$CH$_2$N(CH$_3$)$_2$, there is produced respectively a 5,6-dihydro-12-R-benzo[5,6]cyclohepta[1,2-c]pyridin-6,11-imine, of formula

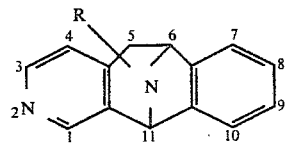

wherein R is as defined immediately above.

EXAMPLE 3

11-Methyl-5,6-dihydrobenzo[5,6]cyclohepta[1,2-c]pyridin-6,11-imine and hydrogen fumarate salt

Step A: Preparation of 5-bromobenzo[5,6]cyclohepta[1,2-c]pyridin-11-one

Bromine (4.18 ml.) in acetic acid (50 ml.) is added dropwise to a stirred solution of benzo[5,6]cyclohepta[1,2-c]pyridin-11-one (12.35 g.) in acetic acid (250 ml.). The resulting mixture is heated on the steam bath for 24 hours and the acetic acid is removed under reduced pressure. Saturated Na$_2$CO$_3$ solution (500 ml.) is added to the residue and the deep yellow solid that forms is collected, washed with water, and dried. This crude product is recrystallized from 1-chlorobutane to give 9.3 g., m.p. 167°–169° C.

Step B: Preparation of 5-bromo-11-methylbenzo[5,6]cyclohepta[1,2-c]pyridin-11-ol Methyl magnesium bromide (27.6 ml., 2.9 M in ether) is added dropwise to a solution of 5-bromobenzo[5,6]cyclohepta[1,2-c]pyridin-11-one (20.02 g., 0.07 mol) in dry THF (300 ml.) with cooling. When addition is complete, the cooling bath is removed and the mixture is stirred for 20–24 hours. The solvent is removed in vacuo, the residue is taken up in water (300 ml.) and acidified by the addition of acetic acid. The solid that forms is collected, washed with water then recrystallized from 2-propanol to give 16.25 g., m.p. 226.5°–229.5° C.

Employing the procedure substantially as described in Step B, but substituting for the 5-bromo compound used as starting material, the 6-methyl compound from Example 1, Step C, there is produced 6,11-dimethylbenzo[5,6]cyclohepta[1,2-c]pyridin-11-ol, m.p. 200°–205° C.

Step C: Preparation of 5-bromo-11-methylenebenzo[5,6]cyclohepta[1,2-c]pyridine The carbinol (6.1 g.) from Step B is dissolved in acetic acid (50 ml.) and concentrated H$_2$SO$_4$ (15 ml.) is added gradually with stirring. After 24 hours the reaction mixture is diluted with H$_2$O (500 ml.) and made alkaline by the addition of 20% NaOH solution. The basic mixture is extracted with ethyl acetate and the combined organic extracts are washed with H$_2$O, saturated NaCl solution, and dried (anhydrous Na$_2$SO$_4$). Removal of the solvent gives 5.65 g. of a dark brown oil.

Step D: Preparation of 6-(4-methylpiperazinyl)-11-methylenebenzo[5,6]cyclohepta[1,2-c]pyridine A mixture of 5-bromo-11-methylenebenzo[5,6]cyclohepta[1,2-c]pyridine (11.0 g.), 1-methylpiperazine (7.8 ml.), potassium tert.-butoxide (8.4 g.) and tert.-butanol (150 ml.) is heated under reflux for 4 hours. The tert.-butanol is removed in vacuo and the residue is taken up in methylene chloride (600 ml.). The resulting mixture is washed with 10% NaCl solution, saturated NaCl solution, and dried (anhydrous Na$_2$SO$_4$). Filtration and removal of the solvent gives 10.76 g. of dark amber oil.

Step E: Preparation of 11-methylenebenzo[5,6]cyclohepta[1,2-c]pyridin-6-one A mixture of the product from Step D (10.76 g.) and 3N HCl (150 ml.) is stirred at room temperature for approximately 24 hours. The dark brown solution is made alkaline by the addition of 20% NaOH solution and extracted with methylene chloride. The extracts are washed with H$_2$O, saturated NaCl solution and dried (Na$_2$SO$_4$). Removal of the solvent in vacuo followed by trituration with petroleum ether (30°–60°) provides 6.2 g., m.p. 98°–110° C.

Step F: Preparation of 11-methylenebenzo[5,6]cyclohepta[1,2-c]pyridin-6-one oxime A mixture of the ketone from Step E (6.2 g.), anhydrous sodium acetate (3.1 g.), hydroxylamine hydrochloride (2.48 g.) and CH₃OH (130 ml.) is heated under reflux for 24 hours. The solvent is removed in vacuo, water (100 ml.) is added to the residue and the resulting yellow-orange solid is collected and dried, 6.4 g., m.p. 183°–205° C. Recrystallization from toluene provides material with m.p. 218.5°–221° C. (dec.).

Step G: Preparation of N-(5-6-dihydro-11-methylenebenzo[5,6]cyclohepta[1,2-c]pyridin-6-yl) hydroxylamine A 10% HCl solution (50 ml.) is added dropwise to a cold (0°–5°) solution of the oxime from Step F (2.6 g.), NaCNBH₃ (5.0 g.), ethanol (50 ml.) and THF (100 ml.). When the acid addition is complete, the cooling bath is removed and the resulting mixture is stirred overnight. The reaction mixture is diluted with H₂O and extracted with ethyl acetate to remove unreacted oxime (recovery 0.7 g.). The resulting aqueous layer is brought to pH 8 with dilute NaOH solution and re-extracted with ethyl acetate. The combined extracts from the basic solution are washed (H₂O, saturated NaCl solution) and dried (Na₂SO₄). Removal of the solvent after filtration gives 1.7 g., yellow solid, m.p. 130°–136°. Recrystallization from ethyl acetate gives material with m.p. 138°–141° C.

Step H: Preparation of 12-hydroxy-11-methylbenzo[5,6]cyclohepta[1,2-c]pyridin-6,11-imine A mixture of the N-substituted hydroxylamine from Step G (1.8 g.) and toluene (40 ml.) is heated to reflux for four and one-half hours. The solvent is removed under reduced pressure and the residue is chromatographed over silica gel. After removal of some by-products with methylene chloride (1)/ethyl acetate (1), the product is eluted with ethyl acetate. Removal of the solvent gives 1.4 g. of light yellow flakes.

Step I: Preparation of 5,6-dihydro-11-methylbenzo[5,6]cyclohepta[1,2-c]pyridin-6,11-imine hydrogen fumarate.

A mixture of the product from Step H (1.4 g.), zinc dust (1.4 g.), and acetic acid (40 ml.) is heated to 80°–100° C. for 4 hours. The reaction mixture is cooled, diluted with H₂O (300 ml.) and filtered. The filtrate is made alkaline with 20% NaOH solution and extracted with ethyl acetate. The ethyl acetate extracts are washed with saturated NaCl solution and dried (Na₂SO₄). Removal of the solvent gives 1.1 g. of a straw-colored foam. This material is converted to its fumarate salt by treatment with 1.1 g. of fumaric acid in 150 ml. of boiling acetone, and gives 1.3 g., of 5,6-dihydro-11-methylbenzo[5,6]cyclohepta[1,2-c]pyridine-6,11-imine hydrogen fumarate, m.p. 194°–195.5° C.

Employing the procedure substantially as described in Example 3, but using as starting material, benzo[5,6-]cyclohepta[1,2-c]pyridin-11-one or the 9-bromo or 9-fluoro derivative thereof and using a Grignard reagent of formula R²MgX wherein X is Br or Cl, in Step B there is produced the 11-R²-5,6-dihydrobenzo[5,6]cyclohepta[1,2-c]pyridin-6,11-imines described in Table III by the following process:

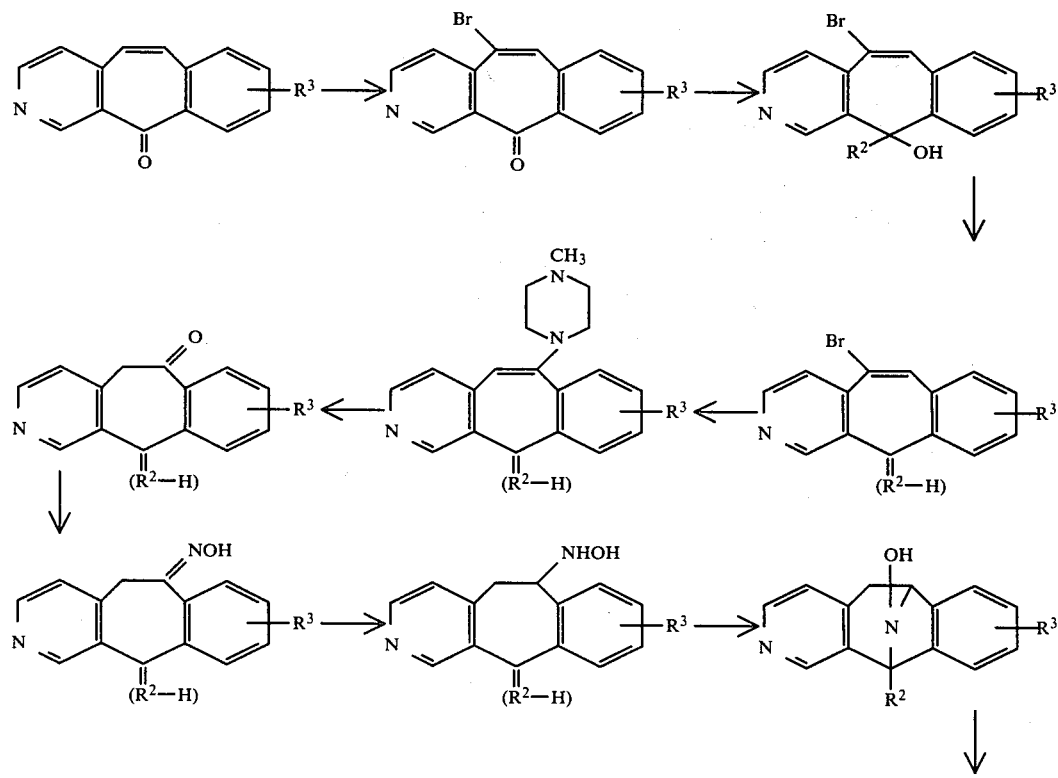

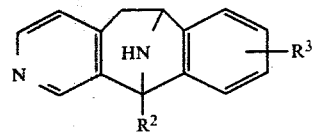

TABLE III

| R² | R³ |
|---|---|
| CH₃— | 9-Br |
| CH₃— | 9-F |
| C₂H₅— | H |
| CH₂=CHCH₂— | 9-F |
| ⌬—CH₂— | H |
| cyclohexyl— | 9-Br |
| cyclopropyl (△) | H |
| △—CH₂— | 9-Br |
| cyclohexyl—CH₂— | H |

TABLE IV

| R | X | R² | R³ |
|---|---|---|---|
| ⌬—CH₂ | Cl | —CH₃ | H |
| C₂H₅— | Br | —CH₃ | H |
| CH₂=CHCH₂— | Br | —CH₃ | 9-Br |
| C₂H₅— | Br | —C₂H₅ | H |
| C₂H₅— | Br | —CH₃ | 9-F |
| C₂H₅— | Br | —CH₃ | H |
| cyclohexyl— | Br | —CH₃ | H |
| △—CH₂— | Br | —CH₃ | H |
| (CH₃)₂NCH₂CH₂CH₂— | Br | —CH₃ | H |
| CH₃— | I | —CH₃ | 9-Br |
| CH₃— | I | —CH₃ | H |

EXAMPLE 4

12-Allyl-5,6-dihydro-11-methylbenzo[5,6]cyclohepta[1,2-c]pyridin-6,11-imine

A mixture of 2.45 g. of 5,6-dihydro-11-methylbenzo[5,6]cyclohepta[1,2-c]pyridin-6,11-imine, 1.8 g. of allyl bromide, 3.0 g. of anhydrous sodium carbonate and 50 ml. of dry toluene is heated at 80° C. for 20 hours. The mixture is filtered and the filtrate is evaporated in vacuo to give 12-allyl-5,6-dihydro-11-methylbenzo[5,6]cyclohepta[1,2-c]pyridin-6,11-imine which is converted to its hydrogen fumarate salt.

Employing the procedure substantially as described in Example 4, but using a starting materials the benzo[5,6]cyclohepta[1,2-c]pyridin-6,11-imines and the R-halides described in Table IV, there are produced the 12-R-benzo[5,6]cyclohepta[1,2-c]pyridin-6,11-imines also described in Table IV in accordance with the following reaction:

EXAMPLE 5

12-Benzyl-5,6-dihydro-11-methylbenzo[5,6]cyclohepta[1,2-c]pyridin-6,11-imine

To a solution of 5,6-dihydro-11-methylbenzo[5,6]cyclohepta[1,2-c]pyridin-6,11-imine (2.35 g.) and benzaldehyde (1.1 g.) in THF (100 ml.) is added acetic acid (1 ml.) and sodium cyanoborohydride (1.0 g.). The mixture is stirred for two days, filtered and the filtrate evaporated. The residue is slurried with 1N aqueous NH₄OH and extracted with HCCl₃. The chloroform extract is dried over sodium sulfate, filtered and evaporated. The residue is recrystallized from ethanol to yield 12-benzyl-5,6-dihydro-11-methylbenzo[5,6]cyclohepta[1,2-c]pyridin-6,11-imine.

Employing the procedure substantially as described in Example 5 but using as starting materials the benzo[5,6]cyclohepta[1,2-c]pyridin-6,11-imines and the aldehydes described in Table V there are produced the 12-R-benzo[5,6]cyclohepta[1,2-c]pyridin-6,11-imines also described in Table V in accordance with the following reaction:

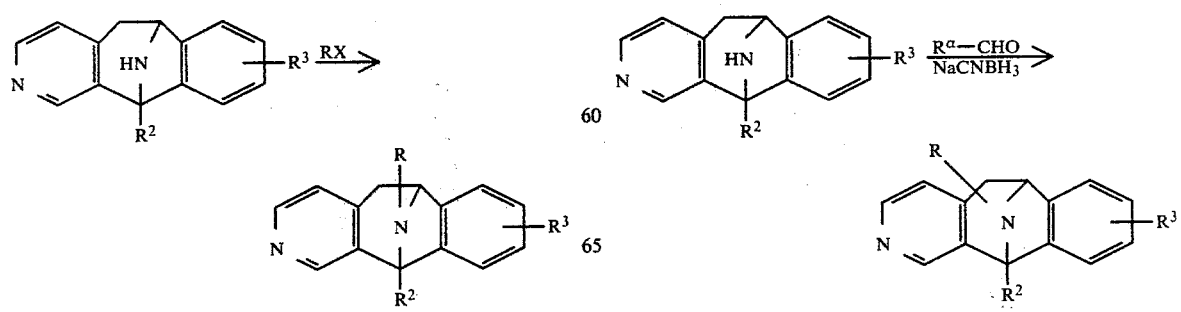

TABLE V

| $R^a$ | R | $R^2$ | $R^3$ |
|---|---|---|---|
| $CH_3$— | —$C_2H_5$ | —$CH_3$ | H |
| $CH_3$— | —$C_2H_5$ | —$CH_3$ | 9-Br |
| $CH_3$ | —$C_2H_5$ | —$CH_3$ | 9-F |

EXAMPLE 6

5,6-Dihydro-12-ethyl-11-methylbenzo[5,6]cyclohepta[1,2-c]pyridin-6,11-imine

An ice cold solution of 5,6-dihydro-11-methylbenzo[5,6]cyclohepta[1,2-c]pyridin-6,11-imine (2.35 g.) and triethylamine (2.0 g.) in ether (100 ml.) is treated dropwise with acetyl chloride (1.5 g.). After 10 hours, the solution is washed with water, dried over sodium sulfate, filtered, and the filtrate evaporated to dryness. The residue is redissolved in ether (200 ml.) and 400 mg. of LiAlH$_4$ added. The resulting slurry is stirred for 24 hours. Water is added slowly and the resulting slurry filtered. The filtrate is dried over sodium sulfate, filtered and the filtrate evaporated to yield 5,6-dihydro-12-ethyl-11-methylbenzo[5,6]cyclohepta[1,2-c]pyridin-6,11-imine.

Employing the procedure substantially as described in Example 6, but using as starting materials the benzo[5,6]cyclohepta[1,2-c]pyridin-6,11-imines and the alkanoyl halides described in Table VI there are produced the 12-R-benzo[5,6]cyclohepta[1,2-c]pyridin-6,11-imines also described in Table VI in accordance with the following reaction:

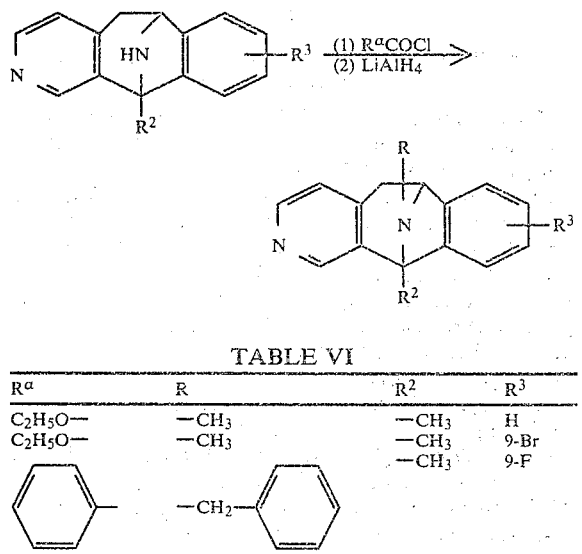

TABLE VI

| $R^a$ | R | $R^2$ | $R^3$ |
|---|---|---|---|
| $C_2H_5O$— | —$CH_3$ | —$CH_3$ | H |
| $C_2H_5O$— | —$CH_3$ | —$CH_3$ | 9-Br |
| ⌬—$CH_2$—⌬ |  | —$CH_3$ | 9-F |

EXAMPLE 7

5,6-Dihydro-6,11-dimethyl-12-phenylbenzo[5,6]cyclohepta[1,2-c]pyridin-6,11-imine A mixture of aniline (1.96 ml.), trifluoroacetic acid (5 ml.) and 6,11-dimethylbenzo[5,6]cyclohepta[1,2-c]pyridin-11-ol is stirred at ambient temperature for 18 hours. It is then heated to reflux with an oil bath for one hour and neutralized. Gas liquid chromatography indicates 11% starting material, 53% 6-methylbenzo[5,6]cyclohepta[1,2-c]pyridin-11-methylene, and 33% 5,6-dihydro-6,11-dimethyl-12-phenylbenzo[5,6]cyclohepta[1,2-c]pyridin-6,11-imine. The title compound is isolated by chromatography on silica gel with equal parts of chloroform and ethyl acetate, and is recrystallized from cyclohexane, m.p. 165°–185° C.

Anal. Calc. for $C_{22}H_{20}N_2$ (312.40): C, 84.58; H, 6.45; N, 8.97.

Found: C, 83.70; H, 6.41; N, 8.94.

EXAMPLE 8

10,11-Dihydro-12-methyl-5H-benzo[4,5]cyclohepta[1,2-b]pyridin-5,10-imine

Step A: Preparation of 5-methylamino-5H-benzo[4,5]cyclohepta[1,2-b]pyridine

Methylamine (3.72 g., 0.12 mole) is added to a mechanically stirred mixture of benzo[4,5]cyclohepta[1,2-b]pyridin-5-one (6.0 g., 0.03 mole) in benzene (150 ml.). A solution of TiCl$_4$ (2.1 ml.) in benzene (50 ml.) is added and the mixture is stirred at 25° C. for 18 hours. Anhydrous potassium carbonate is added to the mixture and it is filtered through diatomaceous earth. The filtrate is evaporated to an amber oil (5.47 g.) which is dissolved in acetonitrile (150 ml.). Sodium borohydride (5.47 g., 0.025 mole) is added and the mixture is heated on a steam bath for 1½ hours. Dilute HCl (3N) is added to the cooled reaction mixture and it is evaporated to dryness under reduced pressure. The residue is dissolved in 3N HCl (150 ml.), extracted with ether and the aqueous filtrate is made alkaline by the addition of 40% NaOH solution. The basic material is extracted into CHCl$_3$ and concentrated to an amber oil (3.96 g.). This oil is converted to a hydrochloride salt by treatment with ethanolic hydrogen chloride for use in Step B.

Step B: Preparation of 10,11-dihydro-12-methyl-5H-benzo[4,5]cyclohepta[1,2-b]pyridin-5,10-imine An ethanol solution of the hydrochloride salt of 5-methylamino-5H-benzo[4,5]cyclohepta[1,2-b]pyridine from Step A is heated in an oil bath (90° C.) for three days. The cooled solution is evaporated to dryness and the resultant foam is dissolved in water (50 ml.). The aqueous solution is extracted with ether and then made alkaline by the addition of 20% NaOH solution. The basic material is extracted into CHCl$_3$ and concentrated to an amber oil (2.90 g.). Silica gel chromatography provides the product as a yellow crystalline solid (1.33 g.). Recrystallization from hexane gives 10,11-dihydro-12-methyl-5H-benzo[4,5]cyclohepta[1,2-b]pyridin-5,10-imine, m.p. 113°–115° C.

Employing the procedure substantially as described in Example 8, Steps A and B but substituting for the methylamine used in Step A, an equimolecular amount of an amine of formula R—NH$_2$, wherein R is

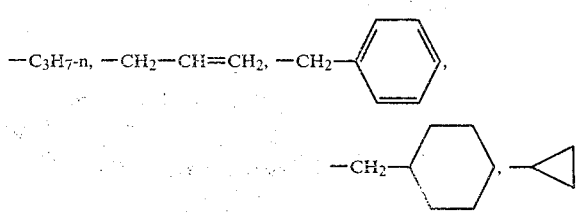

or —CH₂CH₂CH₂N(CH₃)₂ there is produced respectively a 10,11-dihydro-12-R-benzo[4,5]cyclohepta[1,2-b]pyridin-5,10-imine, of formula

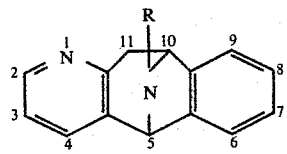

wherein R is as defined immediately above.

EXAMPLE 9

5,6-Dihydro-12-methyl-11H-benzo[5,6]cyclohepta[1,2-b]pyridin-5,11-imine

Step A: Preparation of 5,6-dibromo-5,6-dihydrobenzo[5,6]cyclohepta[1,2-b]pyridin-11-one To a solution of benzo[5,6]cyclohepta[1,2-b]pyridin-11-one (5.20 g., 0.025 mole) in chloroform (100 ml.) is added pyridine perbromide (12.0 g., 0.050 mole). The resultant solution is allowed to stir at 25° C. for 24 hours, and then is heated on the steam bath for 24 hours. Evaporation to dryness produces an amber residue. This residue is taken up in water (100 ml.), make alkaline with saturated sodium carbonate solution, and the basic material is extracted into CHCl₃. The CHCl₃ is removed in vacuo, and the residual oil is triturated with acetone (20 ml.) to yield the product as a brown solid, m.p. 148°–158° C. (dec.).

Step B: Preparation of 6β-bromo-5,6-dihydro-11α-hydroxy-12-methyl-11H-benzo[5,6]cyclohepta[1,2-b]pyridin-5,11-imine To a solution of 5,6-dibromo-5,6-dihydrobenzo[5,6-]cyclohepta[1,2-b]pyridin-11-one (1.0 g., 0.00273 mole) in tetrahydrofuran (100 ml.) is added a solution of CH₃NH₂ (0.13 g., 0.0041 mole) in tetrahydrofuran (25 ml.). The resulting amber solution is stirred at 25° C. for 24 hours. Methylamine hydrobromide is filtered off and the filtrate is evaporated to dryness to yield the product as a tan solid (0.75 g.). Recrystallization from benzene gives 6-β-bromo-5,6-dihydro-11α-hydroxy-12-methyl-11H-benzo[5,6]cyclohepta[1,2-b]pyridin-5,11-imine, m.p. 143°–145° C. dec.

Step C: Preparation of 6β-bromo-11α-chloro-5,6-dihydro-12-methyl-11H-benzo[5,6]cyclohepta[1,2-b]pyridin-5,11-imine Thionyl chloride (20 ml.) is added to a cooled solution of 6β-bromo-5,6-dihydro-11α-hydroxy-12-methyl-11H-benzo[5,6]cyclohepta[1,2-b]pyridin-5,11-imine (2 g.) in toluene (50 ml.). The temperature of the resulting mixture is raised to ambient temperature and warmed on the steam bath for 0.5 hours. Anhydrous potassium carbonate is added and the mixture filtered. The filtrate is evaporated under reduced pressure to give 6β-bromo-11α-chloro-5,6-dihydro-12-methyl-11H-benzo[5,6]cyclohepta[1,2-b]pyridin-5,11-imine.

Step D: Preparation of 5,6-dihydro-12-methyl-11H-benzo[5,6]cyclohepta[1,2-b]pyridin-5,11-imine The oil obtained in Step C is dissolved in 50 ml. of ethyl acetate, triethylamine (5 ml.) and 0.20 g. of 10% palladium on carbon is added and the mixture is hydrogenated under 40–50 lbs/in² of hydrogen pressure. The catalyst and triethylammonium salts are removed by filtration and the filtrate is evaporated under reduced pressure. The oily residue is chromatographed over silica gel using chloroform as the eluent to give 5,6-dihydro-12-methyl-11H-benzo[5,6]cyclohepta[1,2-b]pyridin-5,11-imine.

Employing the procedure substantially as described in Example 9, but substituting for the methylamine used in Step B thereof, an equimolecular amount of an amine of formula R—NH₂, wherein R is

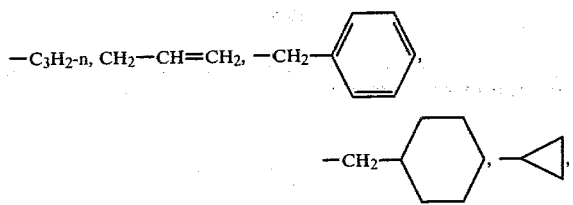

or —CH₂CH₂N(CH₃)₂, there is produced the 5,6-dihydro-12-R-11H-benzo[5,6]cyclohepta[1,2-b]pyridin-5,11-imine in accordance with the following reaction scheme:

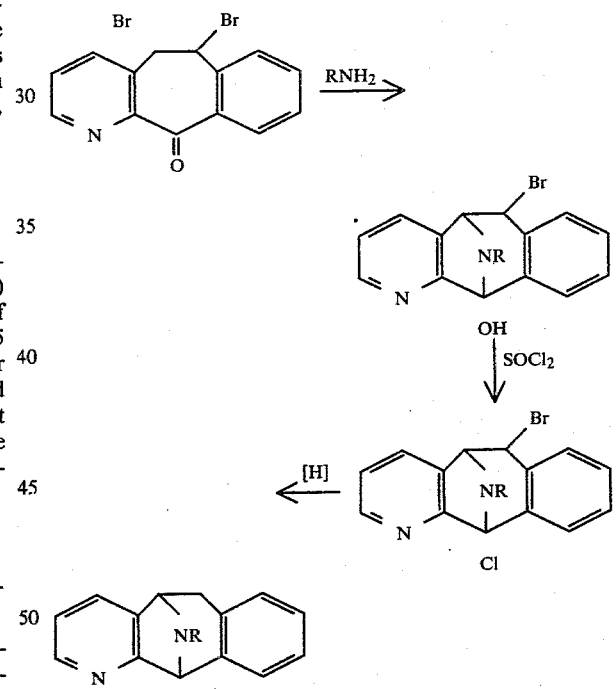

wherein R is as defined immediately above.

EXAMPLE 10

9-Methoxy-5,6-dihydro-6,12-dimethylbenzo[5,6]cyclohepta[1,2-c]pyridin-6,11-imine A mixture of 0.00905 mol. of 9-bromo-5,6-dihydro-6,12-dimethylbenzo[5,6]cyclohepta[1,2-c]pyridin-6,11-imine, 0.181 mole of sodium methoxide, 5.56 g. of electrolytic copper dust, and 87 ml. of dimethylformamide is stirred and heated on a steam bath for 2.5 hours. After cooling, 150 ml. of water and 150 ml. of ether is added to the mixture, and, after stirring, the mixture is filtered through a pad of diatomaceous earth. The ether phase is separated, washed with water, dried over magnesium sulfate, filtered, and the ether is removed on a rotary evaporator. The residue is dissolved in warm acetonitrile. On standing, the solution deposits crystals. The supernatant, containing the desired product, is decanted from the crystals. Evaporation of the solvent gives methoxy-5,6-dihydro-6,12-dimethylbenzo[5,6]cyclohepta[1,2-c]pyridin-6,11-imine.

Employing the procedure substantially as described in Example 10, but substituting for the 9-bromo-5,6-dihydro-6,12-dimethylbenzo[5,6]cyclohepta[1,2-c]pyridin-6,11-imine and sodium methoxide used therein, equimolecular amounts, respectively, of the bromo-compounds and sodium lower alkoxides described in Table VII, there are produced the lower alkoxy-compounds also described in Table VII in accordance with the following reaction:

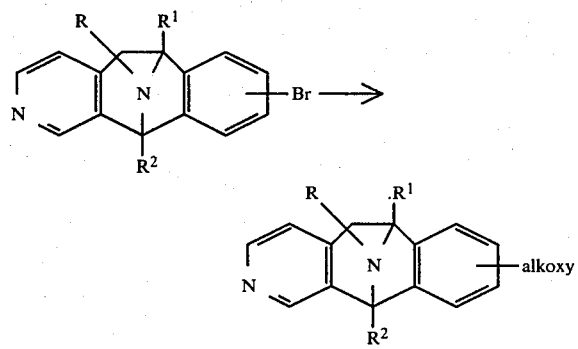

TABLE VII

| R | R¹ | R² | alkoxy |
|---|---|---|---|
| —CH₂CH=CH₂ | n-C₃H₇— | H | 9-OCH₃ |
| —CH₃ | cyclopropyl | H | 9-OCH₃ |
| —CH₂-cyclopropyl | —CH₂-cyclohexyl | H | 9-OC₂H₅ |
| H | H | —CH₃ | 9-OCH₃ |
| H | H | cyclohexyl | 9-OCH₃ |
| H | H | —CH₂-cyclopropyl | 9-OCH₃ |
| CH₂=CHCH₂— | H | —CH₃ | 9-OCH₃ |
| CH₃ | H | —CH₃ | 9-OC₂H₅ |
| C₂H₅ | H | —CH₃ | 9-OCH₃ |

EXAMPLE 11

9-Cyano-5,6-dihydro-6,12-dimethylbenzo[5,6]cyclohepta[1,2-c]pyridin-6,11-imine

A mixture of 0.0249 mole of 9-bromo-5,6-dihydro-6,12-dimethylbenzo[5,6]cyclohepta[1,2-c]pyridin-6,11-imine, 4.58 gm. (0.0498 mole) of cuprous cyanide, and 30 ml. of dry dimethylformamide is stirred and heated under reflux for 6.5 hours. To the cooled solution (25° C.) is added 54 ml. of water, 27 ml. of a saturated aqueous solution of sodium cyanide, and 75 ml. of benzene. The mixture is stirred until a two phase system is obtained. The benzene phase is removed and the aqueous phase is extracted with two 75 ml. portions of benzene. The combined benzene phases are washed with 100 ml. of aqueous 0.1 M sodium cyanide, three 100 ml. portions of water, and dried over magnesium sulfate. After filtering, evaporation of the benzene gives a crystalline residue which is dissolved in the minimum volume of chloroform and passed over an alumina column (15"×1") packed in chloroform. The column is eluted with chloroform. Evaporation of the eluate provides 9-cyano-5,6-dihydro-6,12-dimethylbenzo[5,6]cyclohepta[1,2-c]pyridin-6,11-imine.

Employing the procedure substantially as described in Example 11, but substituting for the 9-bromo-compound used therein, an equimolecular amount of the bromo-compounds described in Table VIII, there are produced the cyano-compounds also described in Table VII in accordance with the following reaction:

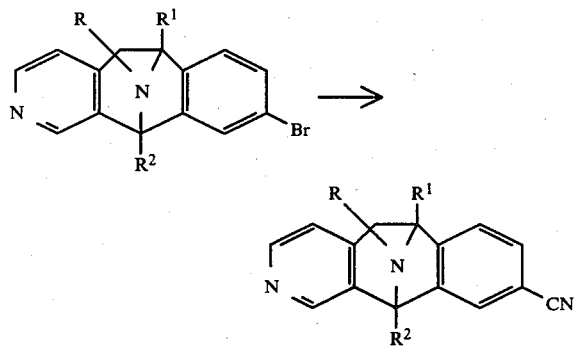

TABLE VIII

| R | R¹ | R² |
|---|---|---|
| —CH₂CH=CH₂ | n-C₃H₇— | H |
| —CH₃ | cyclopropyl | H |
| —CH₂-cyclopropyl | —CH₂-cyclohexyl | H |
| H | H | —CH₃ |
| H | H | cyclohexyl |
| H | H | —CH₂-cyclopropyl |
| CH₂=CHCH₂— | H | —CH₃ |
| CH₃ | H | —CH₃ |
| C₂H₅ | H | —CH₃ |

EXAMPLE 12

9-Carboxy-5,6-dihydro-6,12-dimethylbenzo[5,6]cyclohepta[1,2-c]pyridin-6,11-imine A mixture of 0.00318 ml. of 9-cyano-5,6-dihydro-6,12-dimethylbenzo[5,6]cyclohepta[1,2-c]pyridin-6,11-imine and 20 ml. of 6 N hydrochloric acid is stirred and refluxed for 18 hours. After cooling, the mixture is filtered, and the collected solid is washed with 6 N hydrochloric acid and then with ethanol and dried to give 9-carboxy-5,6-dihydro-6,12-dimethylbenzo[5,6]cyclohepta[1,2-c]pyridin-6,11-imine.

Employing the procedure substantially as described in Example 12, but substituting for the 9-cyano-compound used therein, an equimolecular amount of the cyano-compounds described in Table IX, there are produced the carboxy-compounds also described in Table IX in accordance with the following reaction:

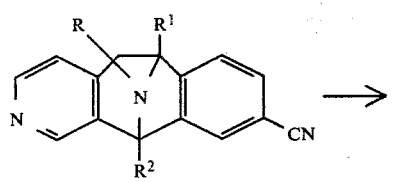

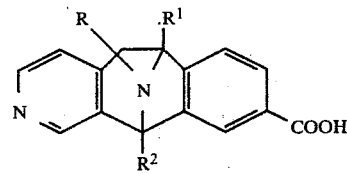

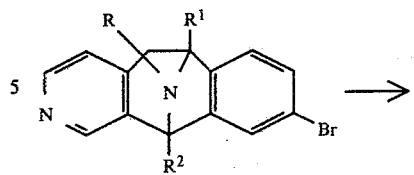

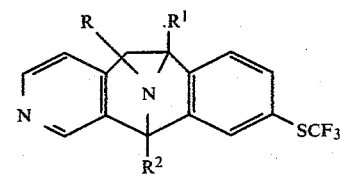

TABLE IX

| R | R¹ | R² |
|---|---|---|
| —CH₂CH=CH₂ | n-C₃H₇— | H |
| —CH₃ | —CH₂-△ | H |
| —CH₂-△ | —CH₂-⬡ | H |
| H | H | —CH₃ |
| H | H | —⬡ |
| H | H | —CH₂-△ |
| CH₂=CHCH₂— | H | —CH₃ |
| CH₃ | H | —CH₃ |
| C₂H₅ | H | —CH₃ |

TABLE X

| R | R¹ | R² |
|---|---|---|
| —CH₂CH=CH₂ | n-C₃H₇— | H |
| —CH₃ | | H |
| —CH₂-△ | —CH₂-⬡ | H |
| H | H | —CH₃ |
| H | H | —⬡ |
| H | H | —CH₂-△ |
| CH₂=CHCH₂— | H | —CH₃ |
| CH₃ | H | —CH₃ |
| C₂H₅ | H | —CH₃ |

EXAMPLE 13

9-Trifluoromethylthio-5,6-dihydro-6,12-dimethylbenzo[5,6]cyclohepta[1,2-c]pyridin-6,11-imine A mixture of 2.24 g. (0.0353 mol.) of copper dust, 3.90 g. (0.97 mol.) of bis-(trifluoromethylthio)-mercury, (0.00484 mol.) of 9-bromo-5,6-dihydro-6,12-dimethylbenzo[5,6]cyclohepta[1,2-c]pyridin-6,11-imine and 20 ml. of dimethylformamide is stirred and heated under reflux for six hours. The mixture is cooled in an ice bath and 100 ml. of chloroform and 30 ml. of concentrated ammonium hydroxide are added. The mixture is stirred overnight at room temperature and is filtered through a pad of diatomaceous earth. The filtrate and chloroform washings are combined and separated from the aqueous phase. The chloroform phase is washed with water, dried over magnesium sulfate, filtered, and the chloroform is removed on a rotary evaporator to give 9-trifluoromethylthio-5,6-dihydro-6,12-dimethylbenzo[5,6-]cyclohepta[1,2-c]pyridin-6,11-imine.

Employing the procedure substantially as described in Example 13, but substituting for the 9-bromo-compound used therein, equimolecular amounts of the bromo-compounds described in Table X, there are produced the trifluoromethylthio-compounds also described in Table X in accordance with the following reaction:

EXAMPLE 14

Preparation of intravenous solutions

A solution containing 10 mg. of 5,6-dihydro-11-methylbenzo[5,6]cyclohepta[1,2-c]pyridin-6,11-imine hydrogen fumarate per ml. of injectable solution is prepared in the following manner.

A mixture of 10 mg. of active ingredient and 9 mg. of sodium chloride is dissolved in sufficient water for injection to make 1 ml. of solution. The pH is adjusted using hydrochloric acid or aqueous sodium hydroxide to about pH 7.0.

If it is desired that the intravenous solution be used for multi-dose purposes, 1.0 mg. of methyl-p-hydroxybenzoate (methyl paraben) and 0.10 mg. of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.1, 1.0, 100.0 mg., respectively, of active ingredient per ml. of solution are similarly prepared substituting the indicated amount for the above-illustrated 10 mg. of quantity. Bulk injectable solutions of convenient volume for subsequent delivery in unit dosage form are readily prepared following the above procedure.

Following the above procedure, other representative injectable solutions of the present invention are prepared when the active ingredient used in 14 is replaced by an equivalent amount of any of the novel compounds of the present invention.

EXAMPLE 15

Tablet Preparation

Tablets containing 1.0, 2.0, 25.0, 26.0, 50.0, and 100.0 mg., respectively, of 5,6-dihydro-11-methylbenzo[5,6-]cyclohepta[1,2-c]pyridin-6,11-imine are prepared as illustrated below.

| TABLE FOR DOSES CONTAINING FROM 1-25 MG. OF THE ACTIVE COMPOUND | | | |
|---|---|---|---|
| | Amount - mg. | | |
| 5,6-dihydro-11-methyl-benzo[5,6]cyclohepta[1,2-c]-pyridin-6,11-imine | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG. OF THE ACTIVE COMPOUND | | | |
|---|---|---|---|
| | Amount - mg. | | |
| 5,6-dihydro-11-methylbenzo-[5,6]cyclohepta[1,2-c]pyridin-6,11-imine | 26.0 | 50.0 | 100.0 |
| Microcrystalline cellulose | 25.0 | 100.0 | 200.0 |
| Modified food corn starch | 2.21 | 4.25 | 8.5 |
| Magnesium stearate | .39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg., 2.0 mg., 25.0 mg., 26.0 mg., 50.0 mg., and 100.0 mg. of active ingredient per tablet. Other tablets are prepared using the same procedures and the equivalent amounts of excipients along with equivalent amounts of any of the novel compounds of the present invention.

What is claimed is:

1. A compound of structural formula:

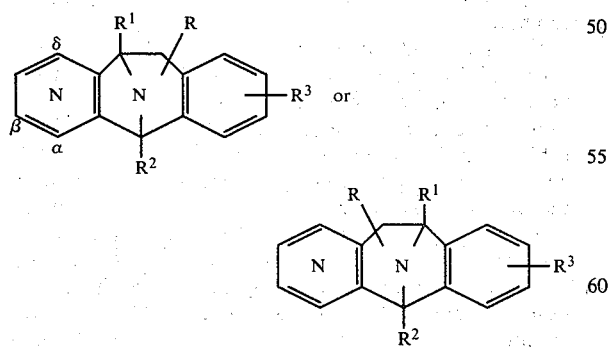

or a pharmaceutically acceptable salt thereof, wherein $R^1$ and $R^2$ are independently
  (1) hydrogen,
  (2) lower alkyl,
  (3) lower alkenyl,
  (4) phenyl-lower alkyl,
  (5) lower cycloalkyl, or
  (6) lower(cycloalkyl-alkyl),
with the proviso that only one of $R^1$ and $R^2$ is other than hydrogen;
R is
  (1) $R^2$,
  (2) phenyl, or
  (3) di(lower alkyl)amino-lower alkyl; and
$R^3$ is
  (1) hydrogen,
  (2) halogen,
  (3) lower alkoxy,
  (4) trifluoromethylthio,
  (5) cyano, or
  (6) carboxy.

2. The compound of claim 1, wherein N of the pyridine ring is in the α, β or δ position.

3. The compound of claim 2, wherein $R^3$ is hydrogen.

4. The compound of claim 3, wherein $R^1$ is hydrogen and R and $R^2$ are independently hydrogen, lower alkyl or benzyl.

5. A pharmaceutical composition comprising a pharmaceutical carrier and an effective amount of a compound of formula:

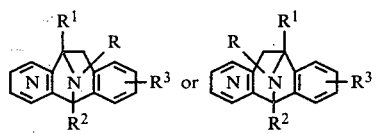

or a pharmaceutically acceptable salt thereof, wherein $R^1$ and $R^2$ are independently
  (1) hydrogen,
  (2) lower alkyl,
  (3) lower alkenyl,
  (4) phenyl-lower alkyl,
  (5) lower cycloalkyl, or
  (6) lower(cycloalkyl-alkyl),
with the proviso that only one of $R^1$ and $R^2$ is other than hydrogen;
R is
  (1) $R^2$,
  (2) phenyl, or
  (3) di(lower alkyl)amino-lower alkyl; and
$R^3$ is
  (1) hydrogen,
  (2) halogen,
  (3) lower alkoxy,
  (4) trifluoromethylthio,
  (5) cyano, or
  (6) carboxy.

6. A method of treating anxiety comprising the administration of an effective amount of a compound of formula:

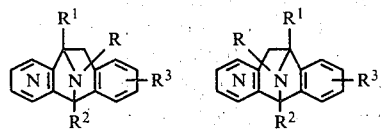

or a pharmaceutically acceptable salt thereof, wherein $R^1$ and $R^2$ are independently
  (1) hydrogen,
  (2) lower alkyl, (3) lower alkenyl,
(4) phenyl-lower alkyl,
(5) lower cycloalkyl, or
(6) lower(cycloalkyl-alkyl),
with the proviso that only one of $R^1$ and $R^2$ is other than hydrogen;

R is
(1) $R^2$,
(2) phenyl, or
(3) di(lower alkyl)amino-lower alkyl; and $R^3$ is
(1) hydrogen,
(2) halogen,
(3) lower alkoxy,
(4) trifluoromethylthio,
(5) cyano, or
(6) carboxy.

* * * * *